US012773534B2

(12) United States Patent
Handberg et al.

(10) Patent No.: US 12,773,534 B2
(45) Date of Patent: Oct. 27, 2026

(54) CATHETER INSTRUMENT

(71) Applicant: Vigmed AB, Helsingborg (SE)

(72) Inventors: Ulf Magnus Handberg, Upplands Väsby (SE); Maria Cecilia Therese Hellström, Lomma (SE)

(73) Assignee: Vigmed AB (SE)

(*) Notice: Subject to any disclaimer, the term of this patent is extended or adjusted under 35 U.S.C. 154(b) by 813 days.

(21) Appl. No.: 18/010,007

(22) PCT Filed: Jun. 17, 2021

(86) PCT No.: PCT/SE2021/050596

§ 371 (c)(1),
(2) Date: Dec. 13, 2022

(87) PCT Pub. No.: WO2022/010396

PCT Pub. Date: Jan. 13, 2022

(65) Prior Publication Data

US 2023/0248947 A1 Aug. 10, 2023

(30) Foreign Application Priority Data

Jul. 7, 2020 (SE) .................................... 2050859-4

(51) Int. Cl.
*A61M 25/06* (2006.01)

(52) U.S. Cl.
CPC .... *A61M 25/0618* (2013.01); *A61M 25/0606* (2013.01)

(58) Field of Classification Search
CPC .......... A61M 25/0606; A61M 25/0612; A61M 25/0618; A61M 25/0631; A61M 25/0693
See application file for complete search history.

(56) References Cited

U.S. PATENT DOCUMENTS 7,972,313 B2 7/2011 Woehr
9,149,625 B2 10/2015 Woehr
9,782,546 B2 10/2017 Woehr
2004/0225260 A1* 11/2004 Villa .................. A61M 5/3273 604/110

(Continued)

FOREIGN PATENT DOCUMENTS

EP 1911485 A1 4/2008
EP 3238770 A1 11/2017

(Continued)

OTHER PUBLICATIONS

Extended EP Search Report, EP21838503.7, dated Jun. 17, 2024.

(Continued)

*Primary Examiner* — Kami A Bosworth
(74) *Attorney, Agent, or Firm* — Fishman Stewart PLLC

(57) ABSTRACT

A catheter instrument and method for assembly extends in a proximodistal direction along a center axis. The catheter instrument comprises a catheter assembly having a catheter hub with a distal end, comprising a high pressure clip provided with an engagement socket, and a needle shielding device having a proximal end comprising a needle protection clip having a proximal engagement portion. The proximal engagement portion engages the socket when the catheter assembly and the needle shielding device are connected to each other.

10 Claims, 10 Drawing Sheets

(56) References Cited

U.S. PATENT DOCUMENTS

| | | | | |
|---|---|---|---|---|
| 2007/0112305 | A1* | 5/2007 | Brimhall | A61M 25/0606 604/164.08 |
| 2008/0140004 | A1 | 6/2008 | Thorne | |
| 2009/0012480 | A1* | 1/2009 | Moulton | A61M 25/0612 604/263 |
| 2014/0276468 | A1 | 9/2014 | Kuehn | |
| 2015/0238733 | A1 | 8/2015 | Bin Abdulla | |
| 2016/0354580 | A1* | 12/2016 | Teoh | A61M 25/0097 |
| 2017/0274183 | A1* | 9/2017 | Burkholz | A61M 5/158 |
| 2018/0256209 | A1* | 9/2018 | Muse | A61M 5/3273 |
| 2018/0289388 | A1 | 10/2018 | Lenker | |
| 2019/0160264 | A1* | 5/2019 | Isaacson | A61M 5/3243 |
| 2019/0262599 | A1* | 8/2019 | Nakagami | A61M 39/1011 |

FOREIGN PATENT DOCUMENTS

| | | | |
|---|---|---|---|
| WO | 0245786 | A2 | 6/2002 |
| WO | 2012075421 | A1 | 6/2012 |
| WO | 2016077234 | A1 | 5/2016 |
| WO | 2016142410 | A1 | 9/2016 |
| WO | 2018077748 | A1 | 5/2018 |
| WO | 2018156148 | A1 | 8/2018 |

OTHER PUBLICATIONS

Swedish Search Report, 2050859-4, dated Feb. 5, 2021.
International Search Report, PCT/SE2021/050596, dated Aug. 24, 2021.
Chinese Notice of Allowance, CN202180042359.3, dated Oct. 24, 2025 (w_machine_translation).
India Examination Report, IN202327005131, dated Feb. 24, 2026.

* cited by examiner

CATHETER INSTRUMENT

CROSS-REFERENCE TO RELATED APPLICATIONS

This application is a National Stage Patent Application of International Patent Application No. PCT/SE2021/050596, filed Jun. 17, 2021, which claims the benefit of Sweden Application Serial No. 2050859-4, filed Jul. 7, 2020, the contents of each are incorporated by reference in their entireties.

TECHNICAL FIELD

The present disclosure relates to a catheter instrument comprising a high pressure clip and a needle clip. Further, the disclosure relates to a method for manufacturing said catheter instrument, a high pressure clip and a catheter hub.

BACKGROUND

Intravenous catheters are used to administer fluids and/or drugs to patients regularly. Fluids are supplied through the catheter through an extension tube, coupled to the catheter through an extension tube coupling present and extending from the catheter hub body. When a catheter instrument is to be applied to a patient, by for instance a caretaker, a needle extending through the catheter tube is used to insert the catheter intravenously. Once the catheter tube is in place, the needle is extracted and the catheter tube remains intravenously.

To protect caretakers and patients from infections caused by potential damages from the needle during the extraction of the needle once the catheter tube is in place, many catheter instruments comprise a needle shield of some sort. The needle shield protects the needle tip and sometimes also covers the needle to avoid spillage of body fluids such as blood.

A common issue with needle shields known in the art is that the needle shielding devices are too long in an axial direction, causing difficulties for the user since the devices are often operated using one hand only. Furthermore, many needle guards rely on automatic mechanisms, e.g. snipping mechanisms, to activate the needle protective shield. The automatic mechanism relies on tensions within the device to trigger the automatic response of the shield. A lot of devices comprises poorly tuned tensions within the device, resulting in a discomforting experience for the patient during use. In addition, several devices have a complex manufacturing process.

Hence, there is an apparent need for an improved catheter instrument having a needle shield which is easier to use, comfortable for the patient and more simple to manufacture.

OVERVIEW

It is an object of the present disclosure, considering the disadvantages mentioned above, to provide a catheter instrument extending in a proximodistal direction along a centre axis A. The catheter instrument comprises a catheter assembly comprising a catheter hub, having a distal end comprising a high pressure clip provided with an engagement socket, and a needle shielding device having a proximal end comprising a needle protection having a proximal engagement portion. The proximal engagement portion engages the socket when the catheter assembly and the needle shielding device are connected to each other. This catheter instrument is advantageous in that is shorter in a longitudinal direction than if a high pressure clip was not part of the catheter instrument. The catheter instrument also provides a more controlled fastening of the needle protection clip to the catheter hub, causing tensions within the needle protection clip to be under control. Further, it is easy to use and to assemble.

In a second aspect, there is provided a method for manufacturing a catheter instrument extending in a proximodistal direction along a centre axis A. The method comprises the steps of providing a catheter assembly comprising a catheter hub having a distal end and providing a needle shielding device having a proximal end, and comprising a needle and a needle protection clip having a proximal engagement portion. The method further comprises joining the catheter assembly and the needle shielding device by mating the proximal end together with the distal end, and inserting a high pressure clip provided with an engagement socket into the catheter hub through an incision provided in the catheter hub. The proximal engagement portion engages the socket when the high pressure clip has been inserted, whereby the catheter assembly and the needle shielding device are connected to each other. This method is beneficial since it provides a catheter instrument having the advantages presented above, and the assembling of the device is facilitated using this method.

In a third aspect, there is provided a high pressure clip comprising a pressure clip base part provided with a socket, and a leg extending from said pressure clip base part. This high pressure clip has the advantage that it provides a dual function. Not only will it provide a socket, which can engage a needle protection clip of a needle shielding device, but the leg extending from the base will also hold a needle septum in place in the catheter hub of a catheter instrument.

In a fourth aspect, there is provided a catheter hub extending along a proximodistal axis A, comprising a distal end provided with an incision in connection with a lumen. This catheter hub is advantageous in that the lumen can hold a high pressure clip as disclosed above, which may be securely fastened by engaging the incision in connection with said lumen.

Further features of the disclosure and its embodiments are set forth in the appended claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which.

DETAILED DESCRIPTION OF THE EMBODIMENTS

Embodiments of the present disclosure will be described in more detail below with reference to the accompanying drawings in order for those skilled in the art to be able to carry out the disclosure. The disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. The embodiments do not limit the disclosure, but the disclosure includes the scope of the appended patent claims. Furthermore, the terminology used in the detailed description of the particular embodiments illustrated in the accompanying drawings is not intended to be limiting of the disclosure.

Embodiments of the present disclosure will now be described below with reference to FIGS. 1 to 7.

Figure 1:
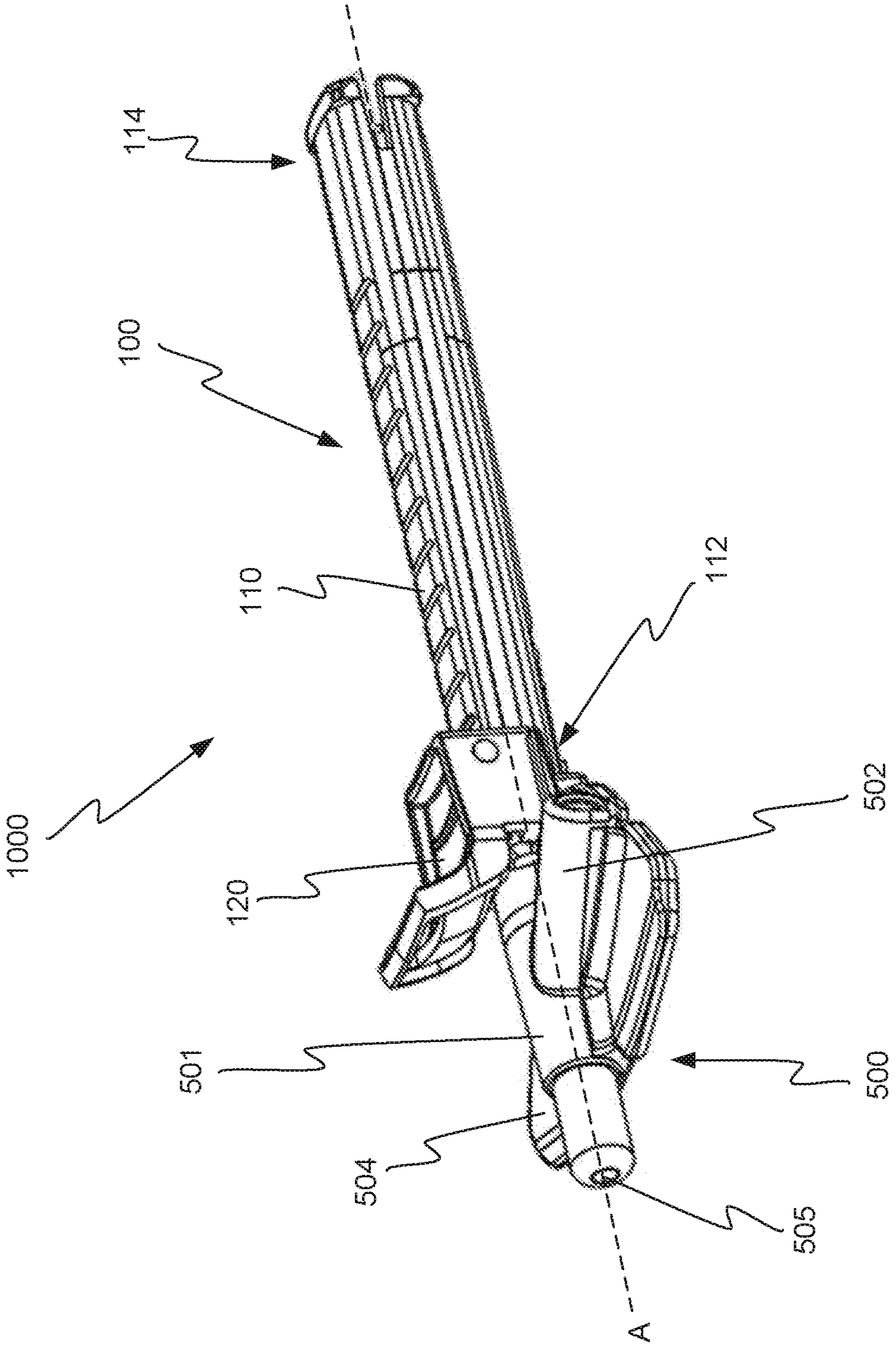
FIG. 1 is an isometric view of a catheter instrument comprising a needle shielding device and a catheter assembly.

Referring to FIG. 1, there is provided a catheter instrument 1000 comprising a needle shielding device 100, and a catheter assembly 500. The needle shielding device 100 shown in FIG. 1 is a part of a telescopic needles shielding device. The catheter instrument 1000 and its parts thereof extend along a longitudinal centre axis A in a proximodistal direction.

The catheter assembly 500 comprises a catheter hub 501, a coupling for an extension tube 502, a pair of wings 504 and an opening 505 configured to hold a hollow catheter tube. The part of the needle shielding device 100 comprises an encapsulation tube 110, a proximal push tab 120 and has a proximal end 112 and a distal end 114. When a needle 150 (shown in FIGS. 2A, 3A and 3B) is extracted from the catheter assembly 500, the encapsulation tube 110 encloses the needle 150.

Figure 2A:
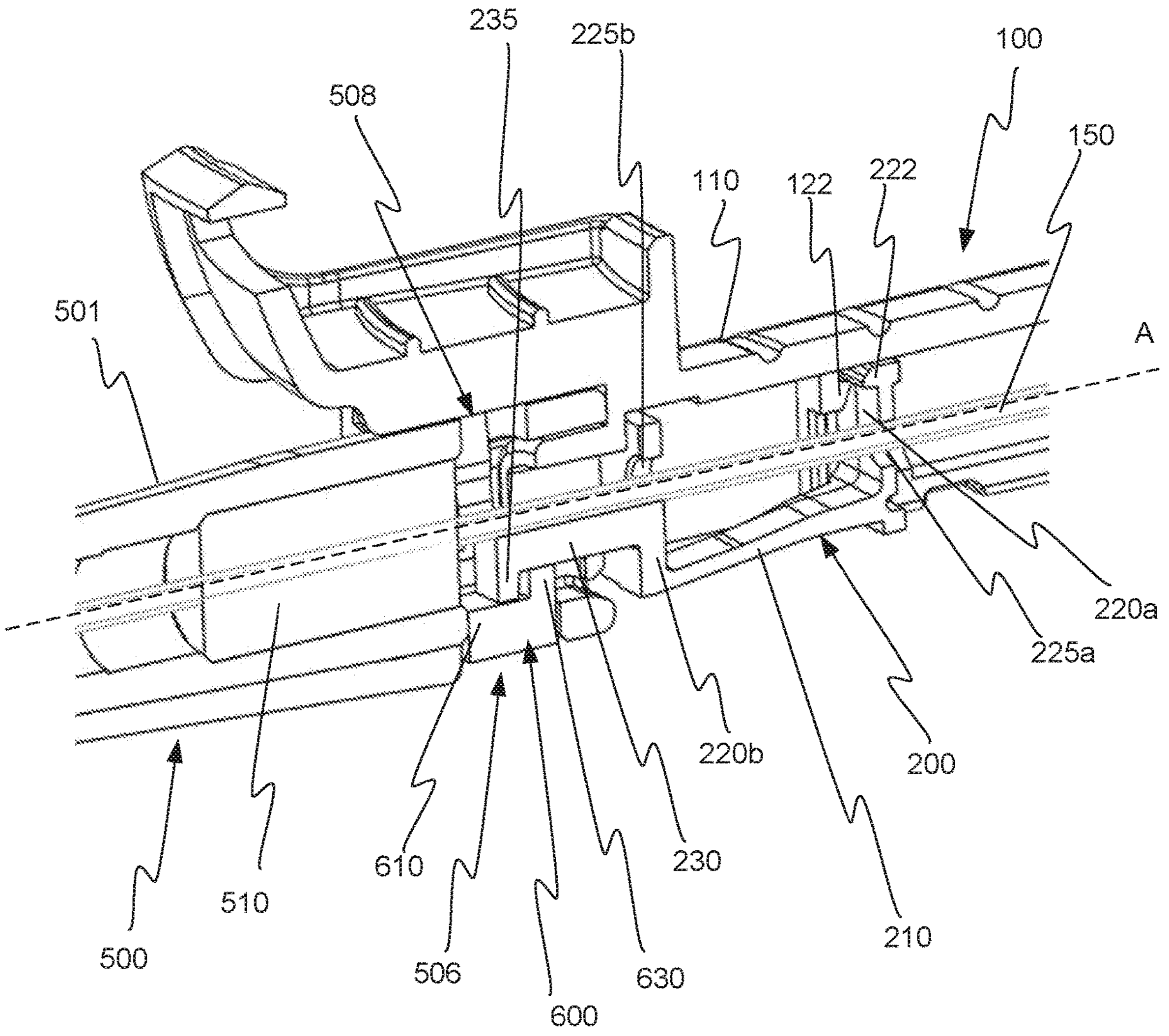
FIG. 2A is a transversal cross-section of a portion of the catheter instrument disclosed in FIG. 1.

FIG. 2A shows a longitudinal cross-section of a portion of the assembled catheter instrument 1000 shown in FIG. 1. The section shown in FIG. 2A is the interface between the catheter assembly 500 and the needle shielding device 100 where the catheter assembly 500 and the needle shielding device 100 are connected to each other. The interior of the catheter assembly 500 comprises a needle septum 510 and a high pressure clip 600. The interior of the proximal end 112 of the needle shielding device 100 comprises a needle protection clip 200 in connecting engagement with the high pressure clip 600. The high pressure clip 600 may also be referred to as a U-lock or septum U-lock herein.

The needle protection clip 200 comprises a lower base part 210, having a transversal distal wall 220*a* and a transversal proximal wall 220*b*, each comprising a distal and a proximal through hole 225*a*, 225*b*, respectively. Further, the clip 200 has a proximally extending arm 230, which in turn comprises a proximal engagement portion 235. The proximal engagement portion 235 is also referred to as a proximal hook 235 herein. Further, the proximal hook 235 extends radially in a lateral direction (substantially perpendicularly to the axis A) away from the centre axis A. Further, the needle shielding device 100 is provided with an internal latch 122 in connecting engagement with a distal wall latch 222 on the protection clip 200. The distal wall latch 222 is arranged on an upper edge of the distal wall 220*a*.

Figure 3A:
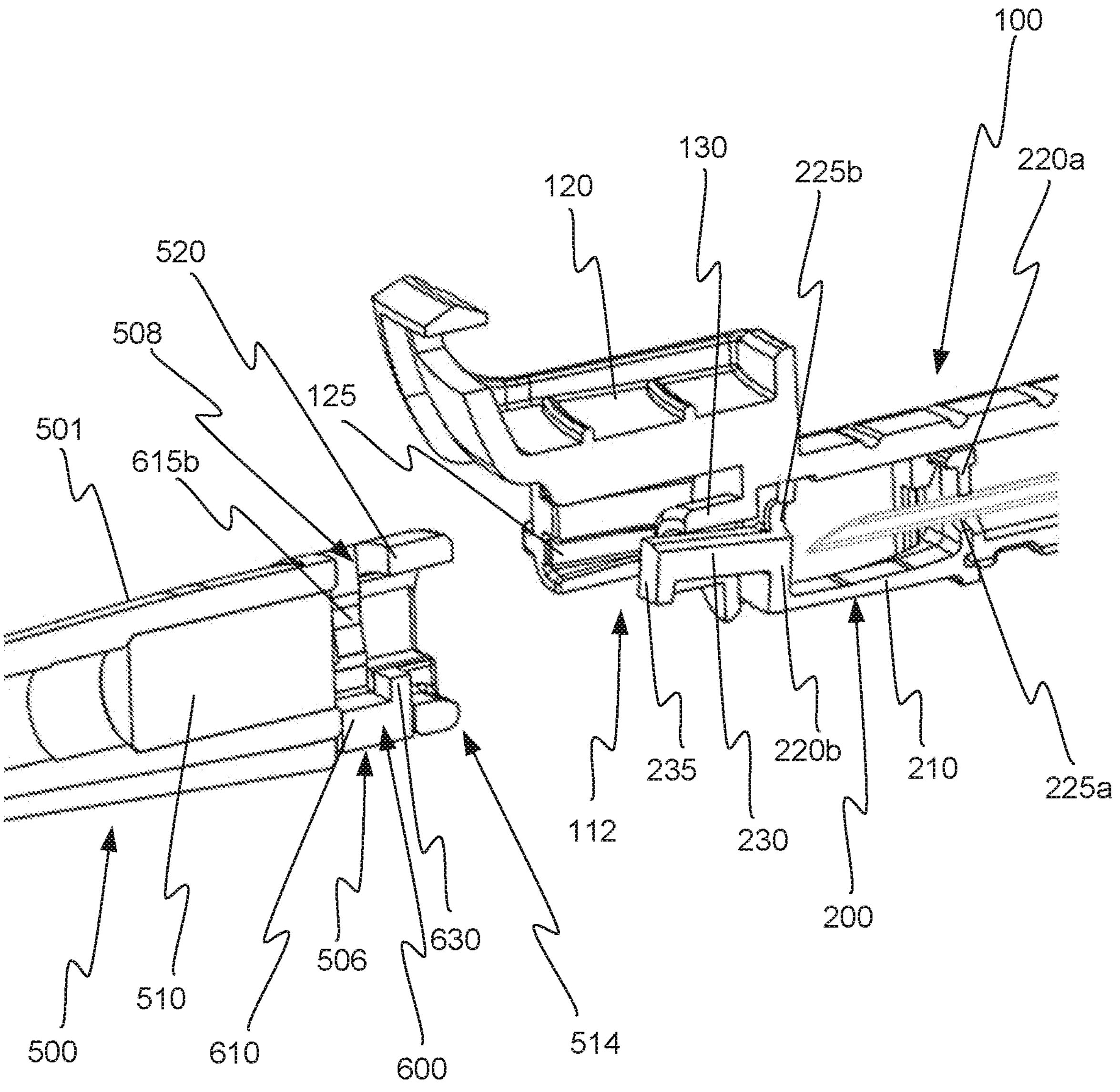
FIG. 3A is a transversal cross-section of a catheter assembly and a needle shielding device detached from each other.

The high pressure clip 600 has a pressure clip base portion 610 from which a distal socket 630 extends centrally towards the centre axis A. As shown in FIG. 2A, the proximal hook 235 of the proximal arm 230 engages the distal socket 630 of the high pressure clip 600. The high pressure clip 600 is fitted into the catheter hub 501 and has been inserted into the catheter assembly 500 from below through a lower incision 506 and two upper incisions 508 in the catheter hub 501 at the catheter assembly distal end 514 (FIG. 3A). The mounting of the catheter instrument 1000 will be explained more in the following with reference to the FIGS. 5, 6A and 6B.

In FIG. 2A (and FIG. 2B) the through holes 225*a*, 225*b* of the distal wall 220*a*, and the proximal wall 220*b* are transversally aligned. A needle 150 extends along the axis A through the aligned through holes 225*a*, 225*b* of the needle protection clip 200, the high pressure clip 600 and the septum 510.

Figure 2B:
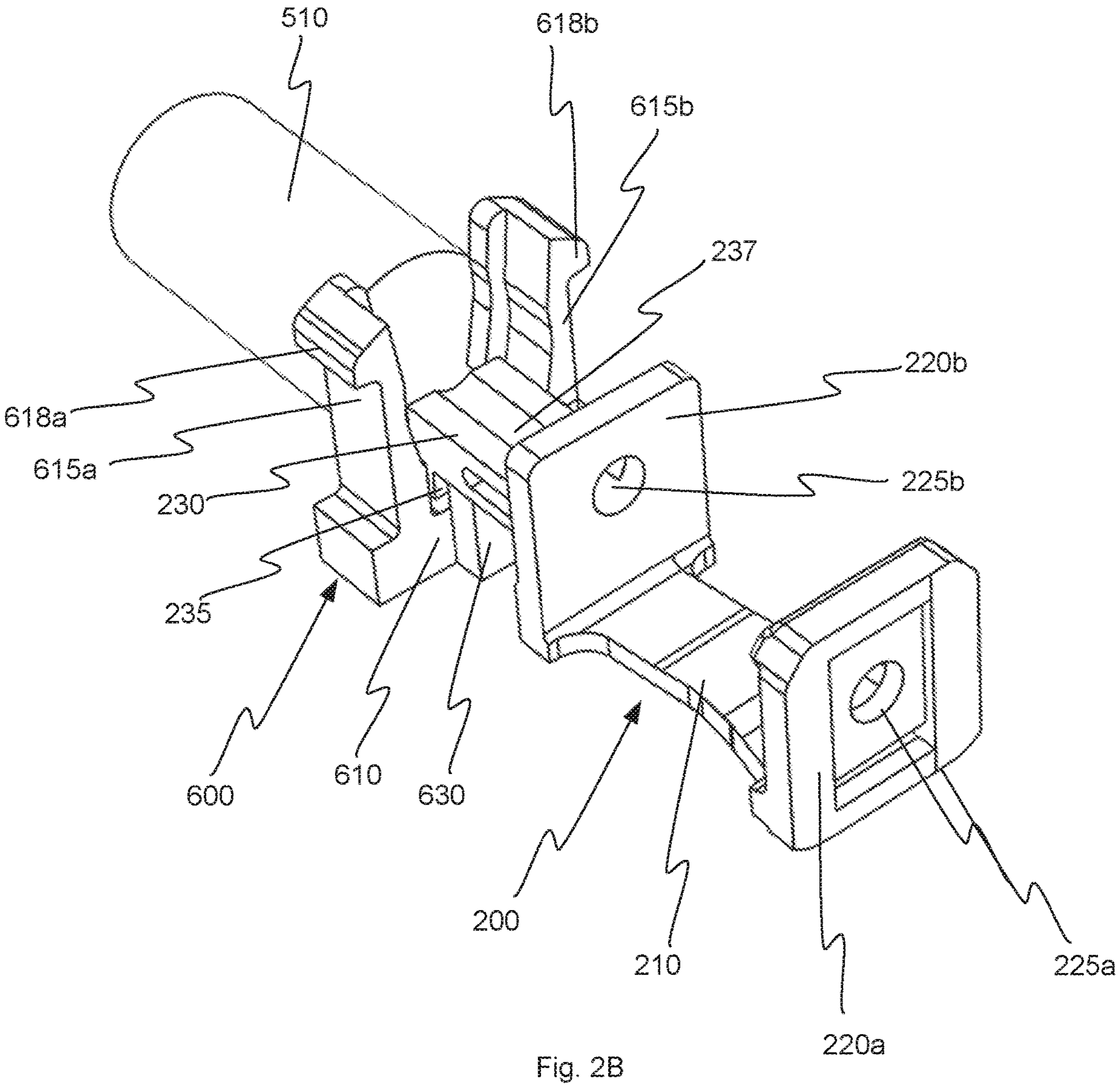
FIG. 2B is an isometric view of a high pressure clip connected to a needle protection clip.

FIG. 2B shows an isometric view of the high pressure clip 600 and the needle clip 200 in engagement with each other. The high pressure clip 600 is arranged in contact with the septum 510 and is fitted in the lower and upper incisions 506, 508 of the catheter assembly 500. The through holes 225*a*, 225*b* of the respective transversal wall 220*a*, 220*b* of the clip 200 are aligned and the proximal hook 235 of the proximally extending arm 230 engages the high pressure clip 600. The needle septum 510 is held in place by the high pressure clip 600, which will be explained in more detail with reference to FIG. 5.

More specifically, the high pressure clip 600 has a protruding socket 630 extending centrally from the high pressure clip base 610. The hook portion 235 of the proximal arm 230 engages the socket 630 when the high pressure clip 600 and the needle clip 200 are attached to each other.

Additionally, the protective needle clip 200 is provided with a needle recess 237 which is configured to hold the needle (shown in FIG. 2A) when it extends through the catheter instrument 1000. Such a needle recess 237 decrease the friction when moving the needle 150 in an axial direction and facilitates the sliding of the needle 150. The high pressure clip 600 further comprises two transversally extending legs 615*a*, 615*b*. Each leg 615*a*, 615*b* is provided with an upper protrusion 618*a*, 618*b*, respectively.

The engaging configuration of the protective needle clip 200 in FIGS. 2A and 2B is not the resting state of the protective clip 200. The needle clip 200 is made of a resilient, flexible material. Preferably, the clip 200 may be made of a polymer, such as a plastic material, or a metal since these materials provide a satisfying flexibility and strength. In the resting state of the protective needle clip 200, the through holes 225*a*, 225*b* are not aligned along the longitudinal axis A, but off-centred transversally in relation to each other.

The needle 150 extending through both through holes 225*a*, 225*b* forces the though holes 225*a*, 225*b* into alignment along the centre axis A, as show in FIGS. 2A and 2B. This is possible due to the flexibility of the protective needle clip 200. Since the distal wall 220*a* is connected to the needle shielding device 100 through the distal wall latch 222, the lower base part 210 is forced downwards when the needle 150 is inserted through both the distal and proximal through holes 225*a*, 225*b*.

With reference to FIG. 3A, the catheter assembly 500 and the needle shielding device 100 have been disconnected from each other. As shown in FIG. 3A, the needle 150 has been retracted from the catheter assembly 500, and has been retracted further distally past the proximal through hole 225*b* of the protective needle clip 200.

Due to that the protective needle clip 200 is formed from a flexible material having a resting state in which the through holes 225*a*, 225*b* are not aligned, the removal of the needle 150 from the proximal through hole 225*b* causes the lower base part 210 to flex towards the centre axis A. This causes misalignment of the through holes 225*a*, 225*b*, which in turn prevents the possibility of the needle 150 being pushed back outside the needle shielding device 100. When the base part 210 moves towards the axis A, the proximal wall 220*b* will abut the tip of the needle 150 if the needle 150 is subsequently pushed in a proximal direction towards the catheter assembly 500.

In addition, the movement of the base part 210 towards the centre axis A cause the hook portion 235 on the arm 230 to disengage from the socket 630 provided on the pressure clip base portion 610 in the interior of the catheter assembly 500. Hence, the needle shielding device 100 detaches from the catheter assembly 500 while at the same time the needle 150 is protected and cannot harm the patient or the caretaker.

Furthermore, below the push tab 120, the proximal end 112 of the needle shielding device 100 is provided with an arm encapsulation part 130, which circumvents the arm 230 of the needle protection clip 200. The push tab 120 is further equipped with side walls, each of which has an inner groove 125, both configured to engage a longitudinal protrusion 525 (shown in FIG. 4) provided on a housing 520 at a distal end 514 of the catheter assembly 500.

One of the legs 615*b* of the high pressure clip 600 is shown in FIG. 3A. The legs 615*a*, 615*b* provide means for connecting the high pressure clip 600 to the catheter assembly 500. In addition, the high pressure clip 600 holds the needle septum 510 in place. These properties of the high pressure clip 600 will be explained in more detail with reference to FIG. 5.

Figure 3B:
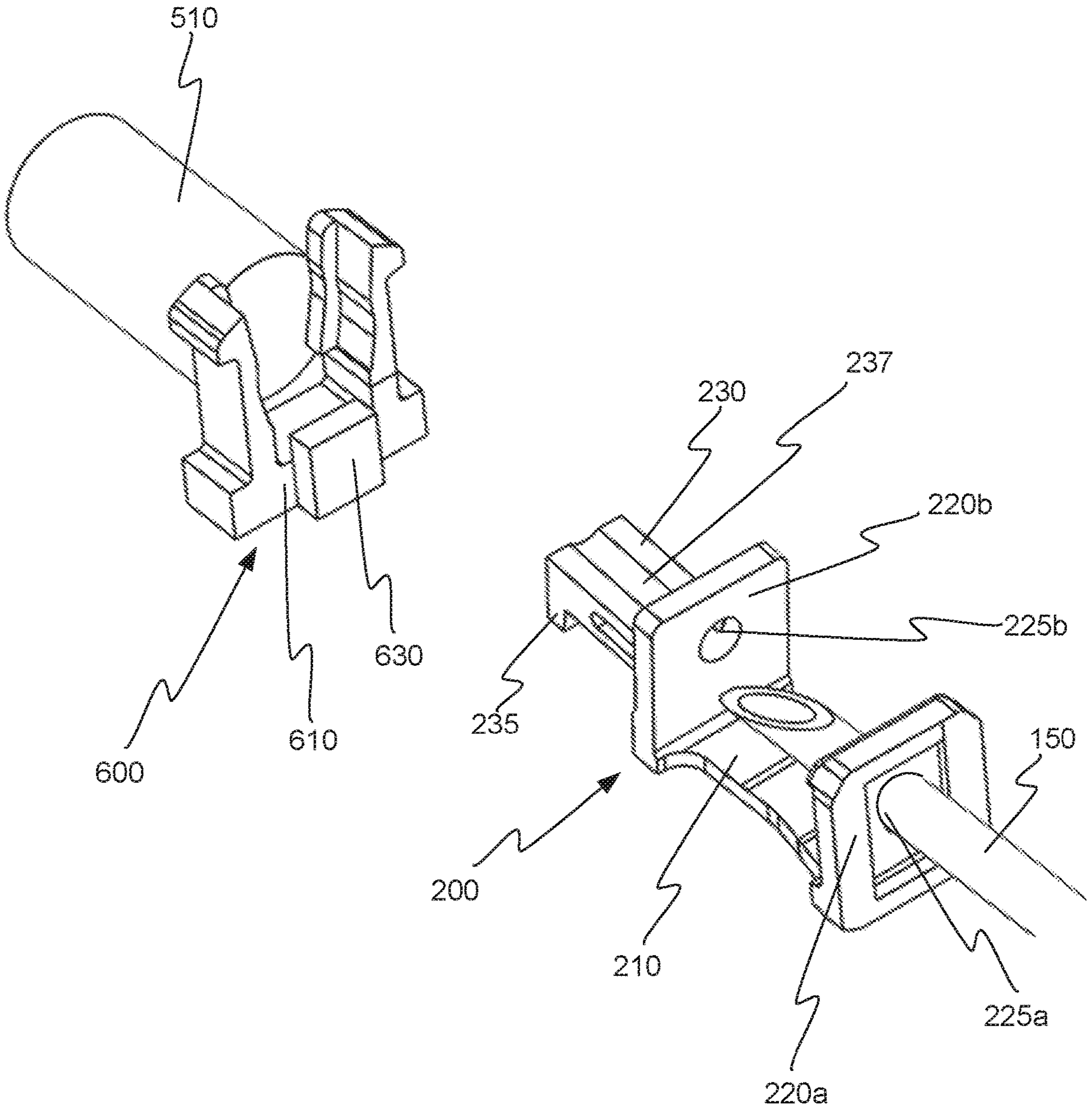
FIG. 3B is an isometric view of the high pressure clip disconnected from the needle protection clip shown in FIG. 2B.

FIG. 3B shows the high pressure clip 600 and the protective clip 200 disengaged from each other. The needle 150 has been retracted distally through the septum 510, the high pressure clip 600 and past the proximal through hole 225*b*. The removal of the needle 150 has caused the arm 230 to flex upwards such that the proximal hook 235 no longer engages the socket 630 on the pressure clip base part 610.

In addition, if the needle 150 is pushed forward in a proximal direction towards the proximal wall 220*b*, the area of the wall 220*b* below the through hole 225*b* will obstruct the needle 150 since the distal through hole 225*a* is no longer aligned with the proximal through hole 225*b*.

Hence, the protective needle clip 200 in the present disclosure has a dual function, it both protects potential users from the needle 150 once it is withdrawn from the catheter assembly 500 and it provides an engagement feature (the proximal hook 235) for connecting the needle shielding device 100 to the catheter assembly 500.

The septum 510 may lack a preformed perforation and may instead be formed from a malleable material which the needle 150 can penetrate, but which will automatically seal when the needle 150 is removed from the septum 510. However, any septum known in the art may be used in the catheter instrument 1000 according to the present disclosure. The needle recess 237 configured to fit the needle 150 facilitates a smooth extraction of the needle 150. The needle recess 237 has a concave shape to hold and fit the needle 150 and decreases the friction between the needle 150 and the proximally extending arm 230.

Figure 3C:
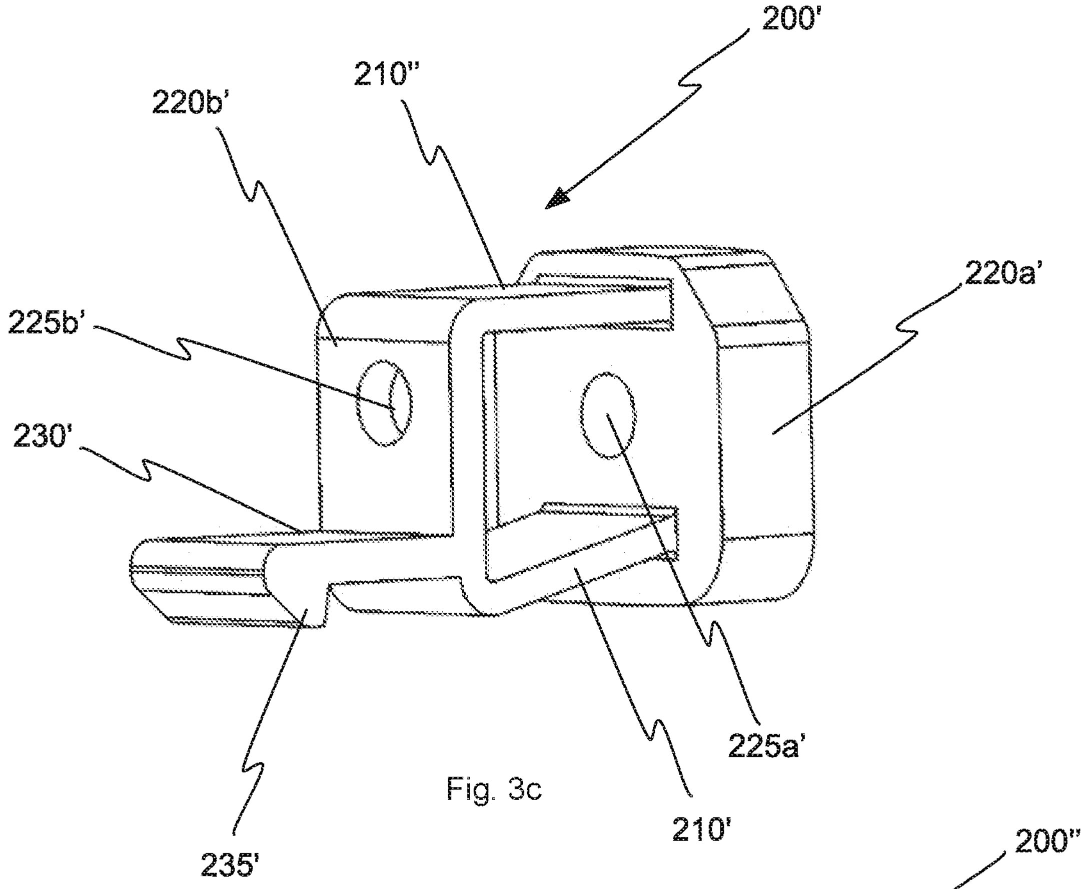
FIGS. 3C and 3D show alternative versions of needle protection clips.
Figure 3D:
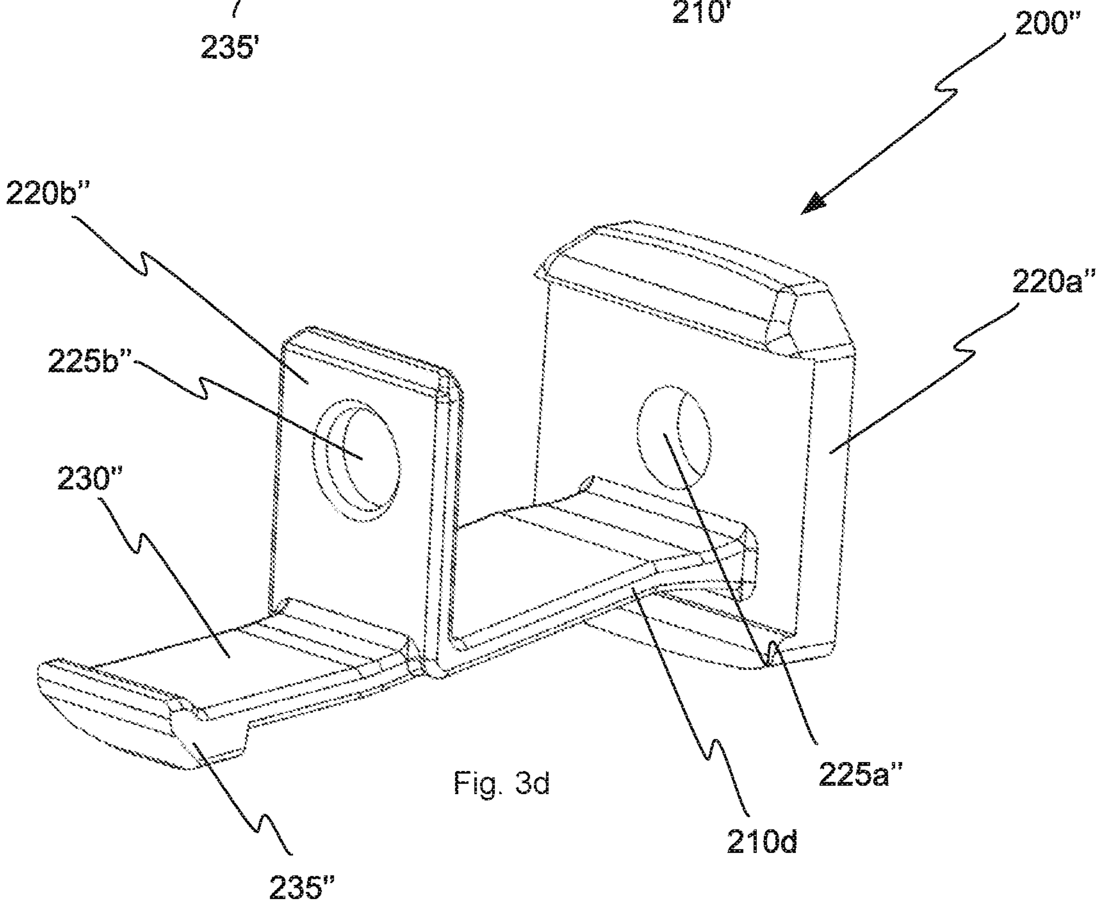

Optionally, the protective needle clip 200 may be an alternative protective needle clip 200' provided with a lower base part 210' and an upper base part 210" as shown in FIG. 3C. Further, in FIG. 3D yet another protective needle clip 200" is shown. The protective needle clips 200', 200" in FIGS. 3C and 3D both have a lower base part 210', 210", a distal wall 220*a*', 220*a*", a proximal wall 220*b*', 220*b*", a distal through hole 225*a*', 225*a*", a proximal through hole 225*b*', 225*b*", an arm 230', 230" and a proximal hook 235".

Further, the protection needle clip 200 may comprise side walls in connection with the base 210 and may be attached to the catheter assembly 500 using other attachment mechanisms or adhesives. The protective needle clip 200' may also be provided with a distal wall latch as the needle protection clip 200 (not shown).

The needle protection clips 200, 200', 200" disclosed herein may be attached to the needle shielding device 100 using an adhesive and the latch 122 and distal wall latch 222 may be arranged on an opposite side of the distal wall 220*a*. Further, the needle protection clips 200, 200', 200" disclosed herein may be attached using any other attachment mechanism suitable within the art.

Figure 4:
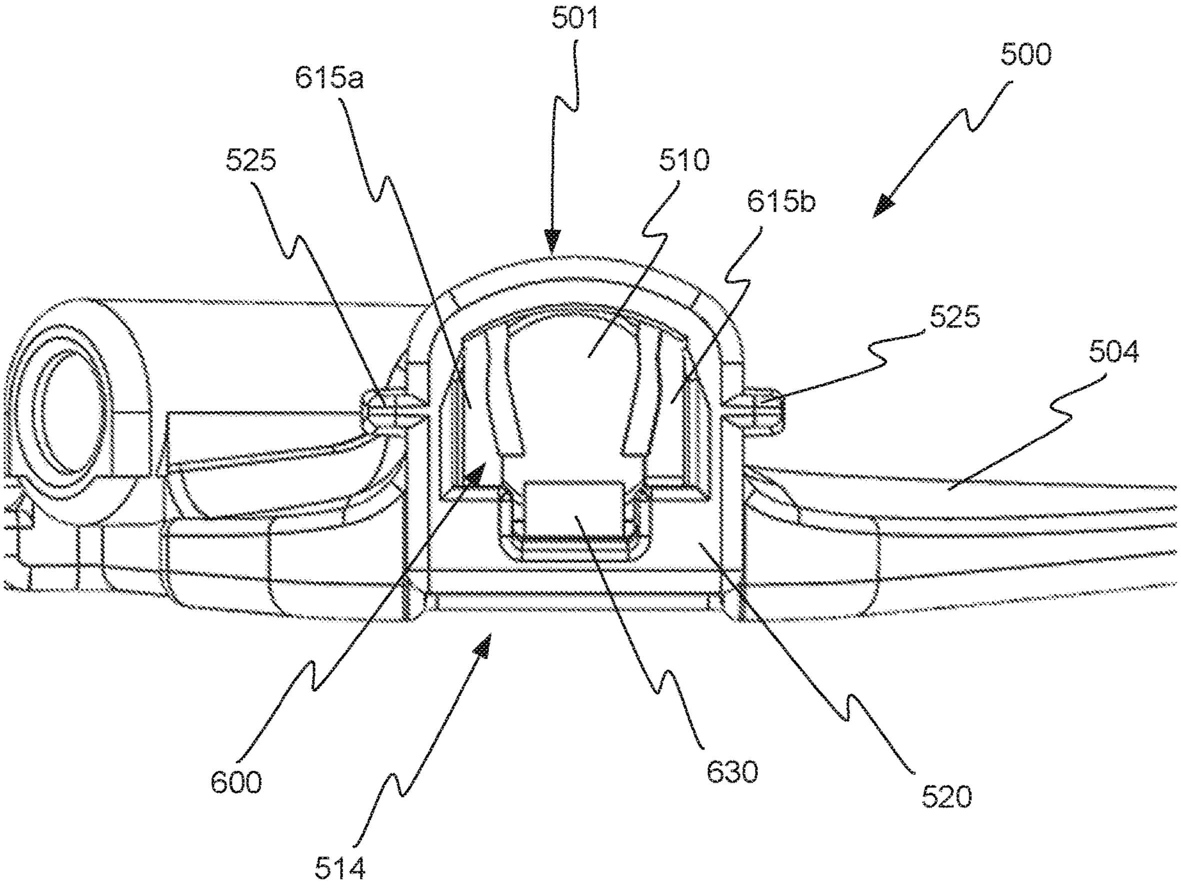
FIG. 4 shows the catheter assembly from a distal perspective.

FIG. 4 shows the catheter assembly 500 viewed from its distal end 514. The distal end 514 of the catheter hub 501 is provided with the housing 520, having two longitudinal protrusions 525 extending along the exterior of said housing 520. The protrusions 525 fit the recesses 125 provided on the interior surface of the side walls below the push button 129 (shown in FIG. 3A). Also, the housing 520 with enclose the arm encapsulation part 130 (also shown in FIG. 3A) when the catheter assembly 500 and the needle shielding device 200 are attached to each other.

Arranged proximally of the housing 520 is the high pressure clip 600, of which the base part 610, the socket 630 and legs 615*a*, 615*b* are visible. Arranged even further inside the catheter hub 501, proximally of the high pressure clip 600, is the needle septum 510.

Figure 5:
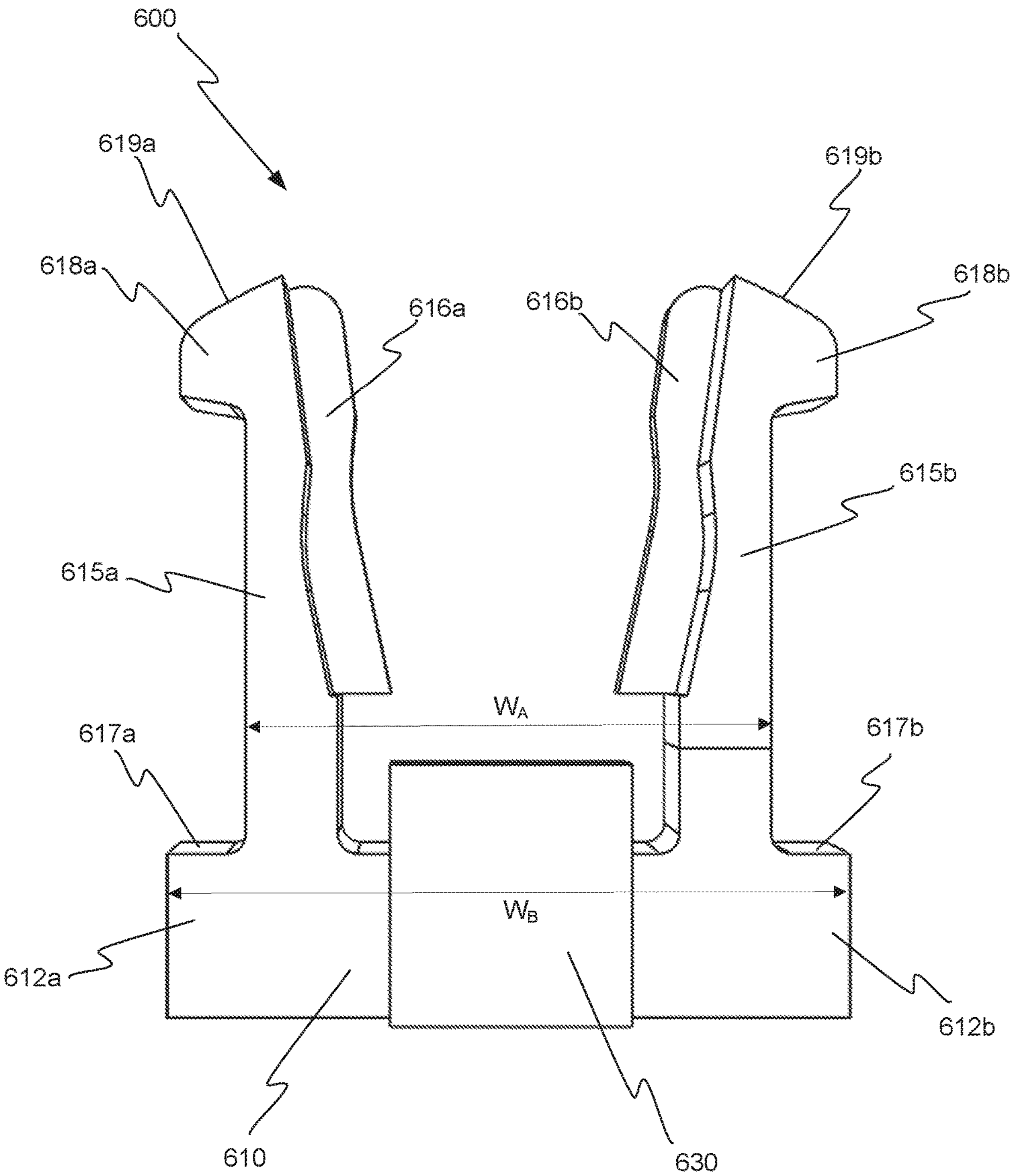
FIG. 5 shows the high pressure clip from a distal perspective.

With reference to FIG. 5, a detailed figure of the high pressure clip 600 in its resting state is shown. The high pressure clip 600 is substantially U-shaped and is made of a slightly flexible material such that the legs 615*a*, 615*b* may flex inwards towards the centre of the U-shaped clip 600. As mentioned with reference to the foregoing FIGS. 1-4, the high pressure clip 600 comprises a base part 610, a socket 630, a pair of legs 615*a*, 615*b* and an upper protrusion 618*a*, 618*b* each arranged on one of the legs 615*a*. 615*b*, respectively. The pressure clip legs 615*a*, 615*b* each has a proximal flange 616*a*, 616*b*, which together lock the septum 510 and hold it in its position proximal of the high pressure clip 600.

Hence, arranging the high pressure clip 600 in the catheter hub 501 has several functions. Firstly, it provides the socket 630 which engages the needle protection clip 200 of the needle shielding device 100, and it locks the needle septum 510 inside the catheter hub 501. In addition, arranging the high pressure clip 600 in the lumen 515 (shown in FIG. 6A) of the catheter hub 501 improves the assembling process of the catheter instrument 1000 to become more simple.

Each upper protrusion 618*a*, 618*b* has an upper side surface 619*a*, 619*b* which are angled downwards in opposite directions, to conform and align with the concave upper surface of the catheter hub 501 when the high pressure clip 600 is assembled in the catheter hub 501. Further, the slightly curved formation of the upper side surfaces 619*a*, 619*b* facilitates the centrally directed flexion of the legs 615*a*, 615*b* when the high pressure clip 600 is pressed against the upper incisions 508. Alternatively, the upper protrusions 618*a*, 618*b* engage on the internal walls of the catheter hub 501. This will be further elaborated with reference to FIG. 6B.

In addition, the high pressure clip 600 comprises two lower protrusions 612*a*, 612*b* extending from the base part 610, in a direction perpendicular to the axis A. Each lower protrusion 612*a*, 612*b* of the base part 610 has a centrally facing upper side surface 617*a*, 617*b*.

Preferably, the high pressure clip 600 is made of a polymeric material (such as a plastic) or a metal material.

Figure 6A:
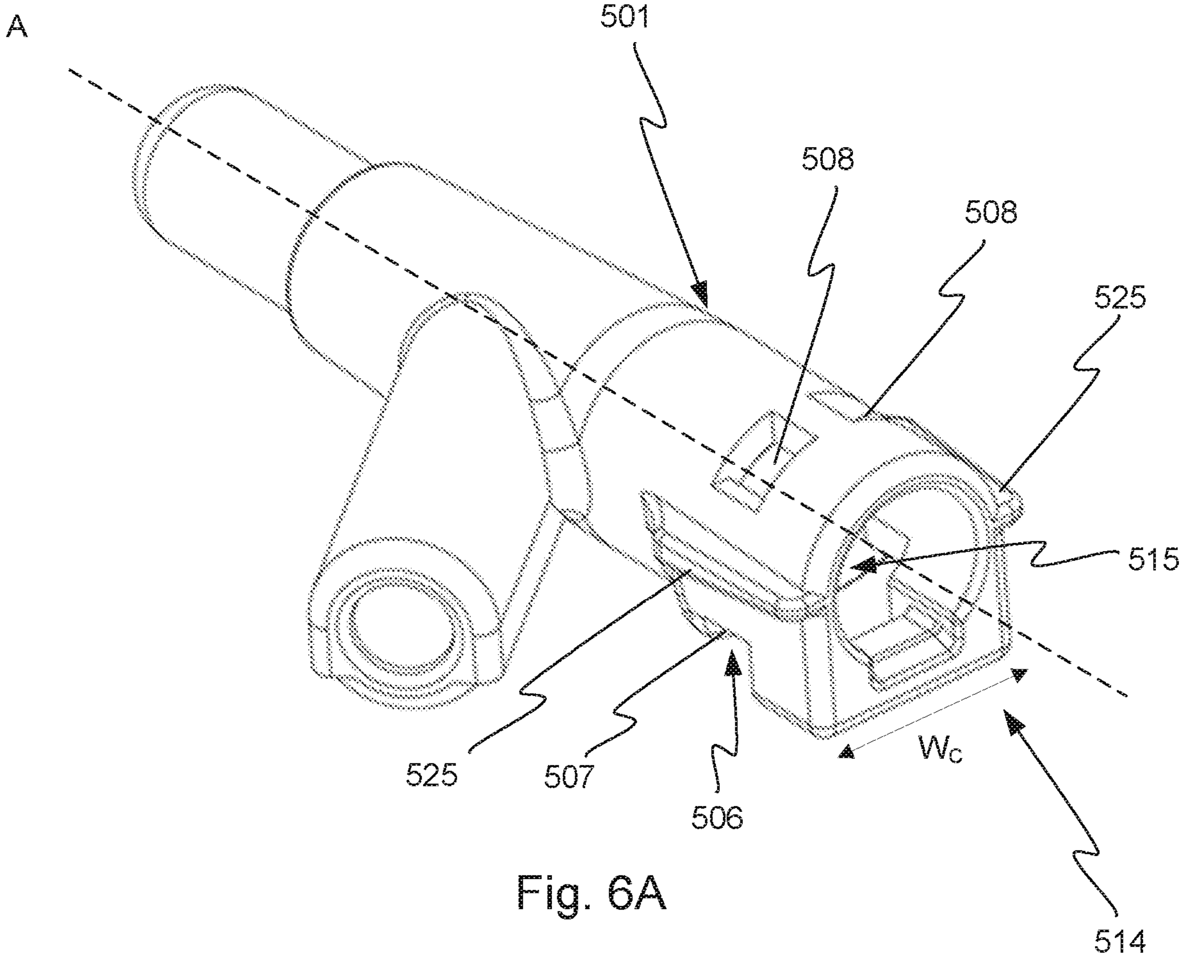
FIGS. 6A and 6B shows isometric views of two embodiments of catheter hubs.

In FIG. 6A, an isometric view of the catheter hub 501 is shown. The catheter hub 501 comprises a distal end 514 and has a width WC. The exterior of the catheter hub 501 is provided with the two longitudinal protrusions 525 and the lower incision 506. The lower incision 506 has a lower incision upper edge 507, and the upper incisions 508 are arranged separately from each other and are aligned transversally perpendicularly of the axis A.

The upper incisions 508 are configured to fit and engage the upper protrusions 618*a*, 618*b* of the high pressure clip 600. The width WB of the pressure clip base part 610 corresponds to the width WC of the catheter hub distal end 514. Further, the area between the lower incision 506 and the upper incisions 598 forms the lumen 515, where the high pressure clip 600 is arranged in the assembled state of the catheter instrument 1000. Further, when the high pressure clip 600 is inserted into the lower incision 506 and forced transversally upwards, the lower protrusions 612*a*, 612*b* of the base part 610 will prevent the high pressure clip 600 from being pushed too far into the lumen 515. The centrally facing upper side surfaces 617*a*, 617*b* will engage the lower incision upper edge 507 and thus prevent the high pressure clip 600 from being forced further into the lumen 515.

Figure 6B:
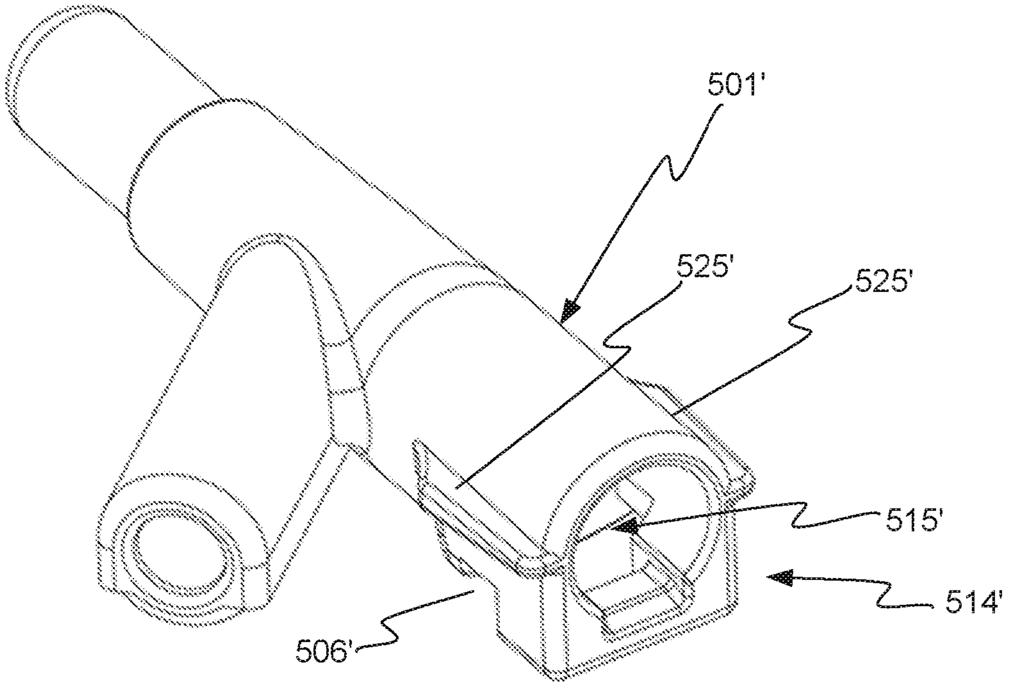

FIG. 6B shows a catheter hub 501' according to another embodiment disclosed herein. The catheter hub 501' comprises a distal end 514', exterior protrusions 525' and a lower incision 506'. However, the catheter hub 501' does not comprise the upper incisions as the catheter hub 501. Instead, the high pressure clip 600 when it is present in the lumen 515 is connected to the catheter hub 501' by other means, for instance the upper protrusions 618*a*, 618*b* each engage in an internal recess inside the catheter hub 501' and is snip-fitted into secure attachment in the lumen 515.

When arranged in the catheter hub 501, the pressure clip base part 610 extends transversally at the bottom of the catheter hub 501 and is fitted in the lower incision 506. The legs 615*a*, 615*b* extends from the base part 610 centrally and further past the central axis A in a lateral direction, along the interior side walls of the catheter hub 501. The upper leg protrusions 618*a*, 618*b* secure the high pressure clip 600 in the catheter hub 501 and prevent extraction of the high pressure clip 600 from the upper incisions 508, the lumen 515 and the lower incision 506.

The use of the high pressure clip 600 in the catheter instrument 1000 disclosed herein provides a catheter instrument 1000 having a more controlled locking mechanism between the needle protection clip 200 and the catheter hub 501 of the catheter assembly 500. This results in controlled tension levels within the needle protection clip 200, which in turn results in a comfortable experience for a patient and a device which is easy to use.

In addition, an effect of the design and arrangement of the high pressure clip 600 in the catheter instrument 1000 disclosed herein is that the needle protection clip 200 can be shortened axially compared to known protection clips. Due to the shorter dimensions of the needle protection clip 200, the length along the axis A of the device is decreased. A shorter device is easier to handle and thus more simple to use, even with a one handed grip.

Figure 7:
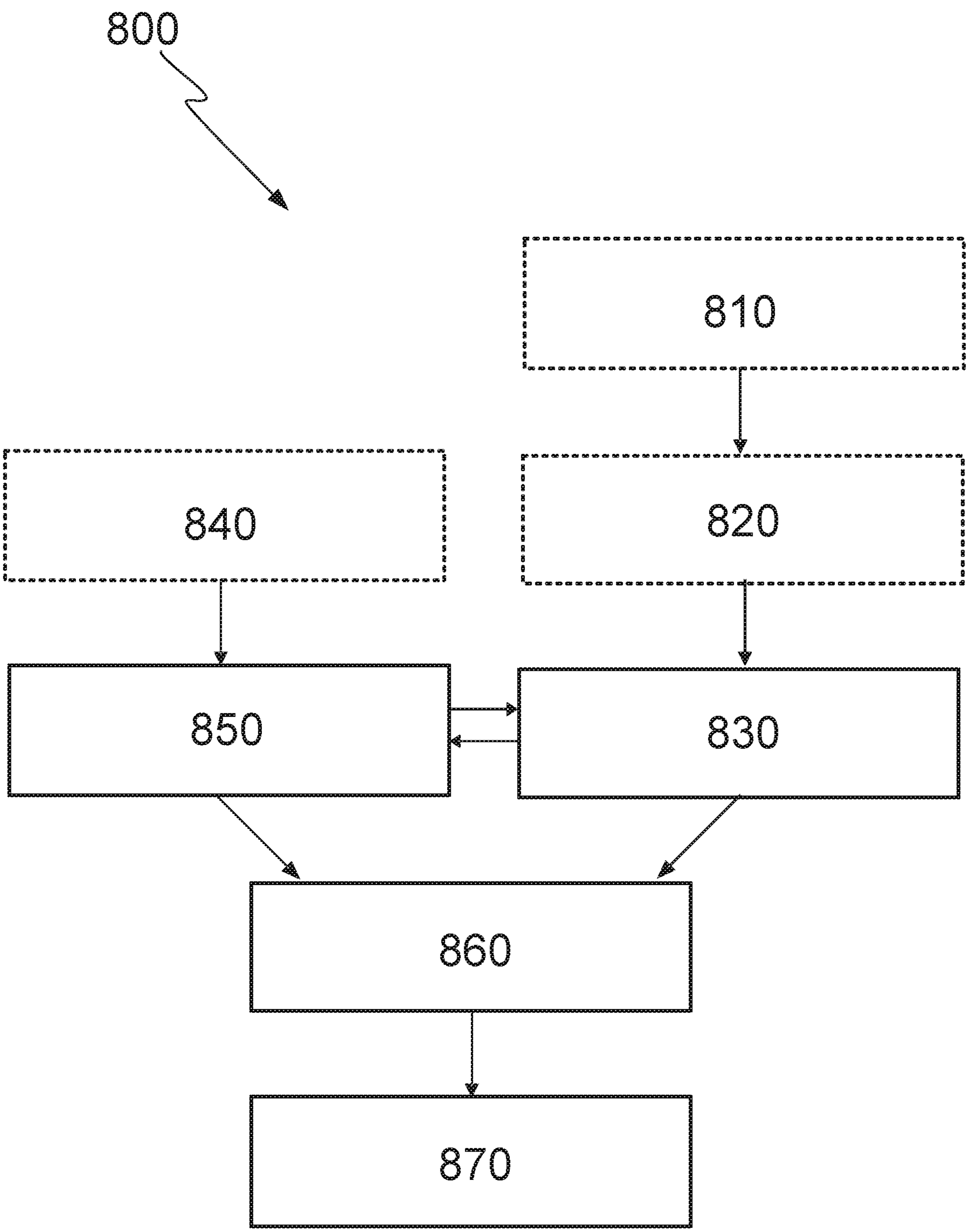
FIG. 7 shows a flow chart of a method for assembling the catheter instrument.

A method for assembling the catheter instrument 1000 will now be explained with reference to the FIGS. 1-6. A flow scheme indicating the steps of the method is shown in FIG. 7. Firstly, the method comprises the step of providing 830 a needle shielding device 100 comprising a needle protection clip 200 and a needle 150. (If the needle shielding device 100 is a telescopic needle shielding assembly as disclosed in SE 2050266-2, the needle 150 is attached to a needle hub in a grip part, which is connected to a telescopic middle part).

Secondly, the method 800 comprises providing 850 a catheter assembly 500. The lumen 515 formed between the lower incision 506 and the upper incision 508 of the catheter assembly 500 is vacant. The catheter assembly 500 may or may not comprise an internal needle septum 510, which has been inserted into the needle hub 501.

The steps of providing 850 a catheter assembly 500 and providing 830 a needle shielding device 100 may occur simultaneously or the step of providing 830 a needle shielding device 100 may be performed before or after the step 850 of providing a catheter assembly 500, as indicated with the arrows between the steps 830 and 850 in FIG. 7.

Optionally, the method comprises a step of engaging 810 the needle 150 with the needle protection clip 200 by threading the needle 150 through the distal and proximal through holes 225*a*, 225*b* in the distal and proximal walls 220*a*, 220*b* before providing 820 the needle shielding device 100.

In yet another optional step, the method 800 comprises attaching 820 (from below in FIG. 2A) the needle protection clip 200 holding said needle 150 into the needle shielding device 100 such that the distal wall latch 222 engages the internal latch 122 with a snip-fit function. (If the needle shielding assembly 100 is a telescopic needle shielding assembly as disclosed in SE 2050266-2, the needle protection clip 200 is inserted into the encapsulation tube 110, which is then moved distally to engage the middle part of the telescopic needle shielding device).

Further, the method 800 may comprise an optional step of mounting 840 a needle septum 510. This step may be performed either by inserting the needle septum 510 inside the catheter hub 501 of the catheter assembly 500 or by threading the needle septum 510 onto the needle 150. If the needle septum 510 is threaded onto the needle 150, the step 840 is performed after the needle protection clip 200 has been threaded onto the needle 150.

The step of mounting 840 the needle septum 510 may occur after or before the step of providing 830 the needle shielding device 100 and/or the step of attaching 840 the needle protection clip 200 in the encapsulation tube 110.

Subsequently, the method comprises joining 860 the needle shielding device 100 and the catheter assembly 500 by pressing the proximal end 112 of the needle shielding device 100 together with the distal end 514 of the catheter assembly 500. The protrusions 525 on the catheter assembly 500 will each engage one of the grooves 125 arranged on the side walls of the push tab 120. Further, the arm encapsulation part 130 will be fitted into the housing 520.

The final step of the method 800 to complete the assembling of the catheter instrument 1000 comprises inserting 870 the high pressure clip 600 into the lower catheter assembly incision 506. The high pressure clip 600 is forced from below through the lower incision 506 transversally upwards such that the leg upper protrusions 618*a*, 618*b* reach the upper incisions 508. The distance between the upper incisions 508 correspond to the width WA between the legs 615*a*, 615*b* of the high pressure clip 600.

Hence, when the upper protrusions 618*a*, 618*b* reach the upper incisions 508 from below, the legs 615*a*, 615*b* will flex inwards, towards the centre axis A. When the upper protrusions 618*a*, 618*b* are forces through the upper incisions 508, the legs 615*a*, 615*b* will spring back to their resting state. As a result, the upper side surface 619*a*, 619*b* of the upper protrusions 618*a*, 618*b* aligns with the upper surface of the catheter hub 501. Thus, the upper protrusions 618*a*, 618*b* engage the upper incisions 508 with a snip fit mechanism, whereby the high pressure clip 600 is securely attached to the catheter hub 501.

The width of the lower incision 506 fits and corresponds to the width WB between the base part lower protrusions 612*a*, 612*b*. The upper incision 506 corresponds to the width WA between the legs 615*a*, 615*b*. Therefore, when the high pressure clip 600 is inserted into the lower incision 506, and when the leg protrusions 618*a*, 618*b* reach the upper incisions 508, the legs 615*a*, 615*b* will flew inwardly towards the centre axis A. When the leg protrusions 618*a*, 618*b* are forced further upwards passed the upper incisions 508 of the catheter hub 501, the legs 615*a*, 615*b* will spring back outwardly to its resting state such that the leg protrusions 618*a*, 618*b* engage in a snip fitting securement with the side edges of the upper incision 508.

Alternatively, the catheter hub 501' is provided with other means for attaching the high pressure clip 600 to the catheter assembly 500.

Optionally, the method further comprises a step of inserting 870 a needle 150 through the catheter instrument 1000, through the proximal and distal through holes 225*a*, 225*b* of the transversal walls 220*a*, 220*b*, the needle septum 510 and the opening 505 into a catheter tube (not shown) as shown in FIG. 2A.

The arrangement of the high pressure clip 600 in the lumen 515 of the catheter hub 501 as disclosed herein facilitates the manufacturing and assembling process. In addition, the length of the overall catheter instrument 1000 is decreased and the tension in the catheter instrument 1000 is relaxed.

For instance, if the catheter instrument 1000 did not comprise the high pressure clip 600, the catheter hub 501 would include a ledge/socket corresponding to the socket 630 of the high pressure clip 600. This would cause the need of flexing the proximally extending arm 230 centrally during the assembling process, which increases the risk of creating fatigue in the arm 230. To avoid fatigue in the material of the arm 230, the arm 230 of the needle protection clip 200 would have to be longer, resulting in an overall longer catheter instrument 1000, which is a disadvantage. By using the high pressure clip 600, the tensions in the needle protection clip 200 is transferred to the lower base part 210, and the risk of causing fatigue in the proximally extending arm 230 is reduced.

The disclosed catheter assembly 500 is a closed system, i.e. a system wherein a septum 510 (shown in FIGS. 2A-3B) is provided in the catheter hub 501, and fluids are withdrawn or introduced through an extension tube (not shown) attached to the extension tube coupling 502. However, the high pressure clip 600 is equally applicable on an open catheter assembly, wherein fluid can be introduced or withdrawn longitudinally from a distal end of the catheter hub, to form a catheter instrument 1000 as disclosed herein.

The needle shielding device 100 disclosed in FIG. 1 is a portion of a telescopic encapsulation shielding assembly, as disclosed in the applicants patent application SE 2050266-2. However, the needle protection clip 200 and high pressure clip 600 may be arranged in other types of needle shielding device.

Further, the high pressure clip 600 may be mounted from a top down direction instead from a bottom up direction, as explained with reference to the figures. Optionally, incisions are present in the side walls of the catheter hub 501 and the legs 615*a*, 615*b* extend from the base part 610 such that the upper protrusions 618*a*, 618*b* are in level transversally with the side wall incisions, and engage said incisions with a snip fit mechanism.

Optionally, the high pressure clip 600 comprises only one laterally extending leg 615*a*, 615*b*. In such case, the single leg 615*a*, 615*b* holds the septum 510 in place. Further, the protrusions 618*a*, 618*b* may be arranged as lower protrusions which attach the high pressure clip to the catheter hub 501 at another position than in the protrusions upper 508.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

The invention claimed is:

1. A catheter instrument extending in a proximodistal direction along a central axis, the catheter instrument comprising:

- a catheter assembly comprising a catheter hub having a distal end comprising a high pressure clip provided with an engagement socket;
- a needle shielding device having a proximal end comprising a needle protection clip having a proximal engagement portion;
- wherein the proximal engagement portion engages the engagement socket when the catheter assembly and the needle shielding device are connected to each other;
- wherein the high pressure clip has a U-like shape comprising a pressure clip base part and a pair of flexible transversally extending legs; and
- wherein each leg comprises an upper protrusion, the catheter hub comprises a pair of upper incisions, and each upper protrusion engages a respective one of the upper incisions of the catheter hub.

2. The catheter instrument according to claim 1, wherein the high pressure clip is arranged in a lumen of the catheter hub.

3. The catheter instrument according to claim 1, wherein the high pressure clip is connected to the catheter hub through a snap fit mechanism.

4. The catheter instrument according to claim 1, wherein the catheter hub has a lower incision and wherein the high pressure clip is arranged in said lower incision.

5. The catheter instrument according to claim 4, wherein the high pressure clip is inserted into the catheter hub from below through said lower incision.

6. The catheter instrument according to claim 1, wherein the needle protection clip comprises a distal through hole and a proximal through hole holding a needle in an assembled state of the catheter instrument, and wherein a base part of the needle protection clip moves towards the central axis when the needle is extracted passed the proximal through hole, whereby the proximal engagement portion detaches from the engagement socket.

7. A method for manufacturing a catheter instrument extending in a proximodistal direction along a central axis, the method comprising:

providing a needle shielding device having a proximal end comprising a needle protection clip having a proximal engagement portion, the needle shielding device further comprising a needle;

providing a catheter assembly comprising a catheter hub having a distal end;

joining the catheter assembly and the needle shielding device by mating the proximal end together with the distal end; and inserting a high pressure clip provided with an engagement socket into the catheter hub through an incision provided in the catheter hub such that the distal end of the catheter hub comprises the high pressure clip;

wherein the proximal engagement portion engages the engagement socket when the high pressure clip has been inserted, whereby the catheter assembly and the needle shielding device are connected to each other;

wherein the high pressure clip has a U-like shape comprising a pressure clip base part and a pair of flexible transversally extending legs; and wherein each leg comprises an upper protrusion, the catheter hub comprises a pair of upper incisions, and each upper protrusion engages a respective one of the upper incisions of the catheter hub.

8. The method according to claim 7, wherein the method further comprises a step of engaging the needle comprised in the needle shielding device with the needle protection clip.

9. The method according to claim 8, further comprising attaching the needle protection clip engaged with said needle into the needle shielding device such that a distal wall latch of the needle protection clip engages an internal latch in the needle shielding device with a snip-fit function.

10. The method according to claim 7, further comprising a step of mounting an internal needle septum inside the catheter hub of the catheter assembly or onto the needle comprised in the needle shielding device.

* * * * *